(12) United States Patent
Rao et al.

(10) Patent No.: US 7,285,690 B2
(45) Date of Patent: Oct. 23, 2007

(54) PROCESS FOR THE PREPARATION OF 1,1,1,3,3-PENTAFLUOROPROPANE AND 1,1,1,3,3,3-HEXAFLUOROPROPANE

(75) Inventors: Velliyur Nott Mallikarjuna Rao, Wilmington, DE (US); Allen C. Sievert, Elkton, MD (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 10/572,627

(22) PCT Filed: Oct. 13, 2004

(86) PCT No.: PCT/US2004/034455

§ 371 (c)(1),
(2), (4) Date: Mar. 17, 2006

(87) PCT Pub. No.: WO2005/037744

PCT Pub. Date: Apr. 28, 2005

(65) Prior Publication Data

US 2007/0123742 A1    May 31, 2007

Related U.S. Application Data

(60) Provisional application No. 60/511,354, filed on Oct. 14, 2003.

(51) Int. Cl.
*C07C 17/00* (2006.01)
*C07C 17/10* (2006.01)

(52) U.S. Cl. .................................... 570/175; 570/176

(58) Field of Classification Search ............... 570/175, 570/176
See application file for complete search history.

(56) References Cited

U.S. PATENT DOCUMENTS

| | | | |
|---|---|---|---|
| 2,942,036 A | 6/1960 | Smith et al. |
| 3,865,885 A | 2/1975 | Bruce, Jr. |
| 3,878,257 A | 4/1975 | Bruce, Jr. |
| 5,036,036 A | 7/1991 | Lerou |
| 5,136,113 A | 8/1992 | Rao |
| 5,171,901 A | 12/1992 | Gassen et al. |
| 5,281,568 A | 1/1994 | Scott et al. |
| 5,414,165 A | 5/1995 | Nappa et al. |
| 5,449,656 A | 9/1995 | Scott et al. |
| 5,545,774 A | 8/1996 | Rao |
| 5,623,092 A | 4/1997 | Scott et al. |
| 5,663,464 A | 9/1997 | Okamoto et al. |
| 5,714,655 A | 2/1998 | Yamamoto et al. |
| 5,763,706 A | 6/1998 | Tung et al. |
| 5,902,911 A | 5/1999 | Rao et al. |
| 5,945,573 A | 8/1999 | Nappa et al. |
| 6,066,769 A | 5/2000 | Nappa et al. |
| 6,291,730 B1 | 9/2001 | Baker et al. |
| 6,376,727 B1 | 4/2002 | Rao et al. |
| 6,403,524 B2 | 6/2002 | Scott et al. |
| 6,540,933 B1 | 4/2003 | Sievert et al. |
| 2001/0011061 A1 | 8/2001 | Scott et al. |

FOREIGN PATENT DOCUMENTS

| | | |
|---|---|---|
| AU | A 94/80340 | 6/1995 |
| DE | 23 58 254 | 6/1975 |
| EP | 0 442 075 | 8/1991 |
| EP | 0 502 605 | 9/1992 |
| EP | 0 611 744 | 8/1994 |
| EP | 0 657 408 | 6/1995 |
| GB | 2 275 924 | 9/1994 |
| WO | WO98/10862 | 3/1998 |
| WO | WO2005/037431 | 4/2005 |
| WO | WO2005/037742 | 4/2005 |
| WO | WO2005/037743 | 4/2005 |

OTHER PUBLICATIONS

U.S. Appl. No. 10/572,626, filed Oct. 13, 2004, Rao et al.
U.S. Appl. No. 10/572,625, filed Oct. 13, 2004, Rao et al.
U.S. Appl. No. 10/572,628, filed Oct. 13, 2004, Amos et al.

*Primary Examiner*—J. Parsa

(57) ABSTRACT

A process for the manufacture of $CF_3CH_2CHF_2$ and $CF_3CH_2CF_3$ is disclosed. The process involves (a) reacting HF and at least one halopropene of the formula $CX_3CCl\!=\!CClX$ (where each X is independently F or Cl) to produce a product including both $CF_3CCl\!=\!CF_2$ and $CF_3CHClCF_3$; (b) reacting $CF_3CCl\!=\!CF_2$ and $CF_3CHClCF_3$ produced in (a) with hydrogen to produce a product including both $CF_3CH_2CHF_2$ and $CF_3CH_2CF_3$; and (c) recovering $CF_3CH_2CHF_2$ and $CF_3CH_2CF_3$ from the product produced in (b). In (a), the $CF_3CCl\!=\!CF_2$ and $CF_3CHClCF_3$ are produced in the presence of a fluorination catalyst including a $ZnCr_2O_4$/crystalline α-chromium oxide composition, a $ZnCr_2O_4$/crystalline α-chromium oxide composition which has been treated with a fluorinating agent, a zinc halide/α-chromium oxide composition and/or a zinc halide/α-chromium oxide composition which has been treated with a fluorinating agent.

7 Claims, No Drawings

PROCESS FOR THE PREPARATION OF 1,1,1,3,3-PENTAFLUOROPROPANE AND 1,1,1,3,3,3-HEXAFLUOROPROPANE

This application represents a national filing under 35 U.S.C. 371 of PCT International Application No. PCT/US2004/034455 filed Oct. 13, 2004, and claims priority benefit of U.S. Application No. 60/511,354 filed Oct. 14, 2003.

FIELD OF THE INVENTION

This invention relates to the synthesis of 1,1,1,3,3-pentaflouropropane and 1,1,1,3,3,3-hexafluoropropane.

BACKGROUND

A number of chlorine-containing halocarbons are considered to be detrimental toward the Earth's ozone layer. There is a world-wide effort to develop materials having lower ozone depletion potential that can serve as effective replacements. For example, the hydrofluorocarbon, 1,1,1,2-tetraflouroethane (HFC-134a) is being used as a replacement for dichlorodifluoromethane (CFC-12) in refrigeration systems. There is a need for manufacturing processes that provide halogenated hydrocarbons that contain less chlorine or no chlorine. The production of hydrofluorocarbons (i.e., compounds containing only carbon, hydrogen and fluorine), has been the subject of considerable interest to provide environmentally desirable products for use as solvents, blowing agents, refrigerants, cleaning agents, aerosol propellants, heat transfer media, dielectrics, fire extinguishants and power cycle working fluids. For example, 1,1,1,3,3-pentafluoropropane has utility as a blowing agent, and 1,1,1,3,3,3-hexafluoropropane has utility as a fire extinguishant and as a refrigerant.

SUMMARY OF THE INVENTION

This invention provides a process for the manufacture of 1,1,1,3,3-pentaflouropropane (HFC-245fa) and 1,1,1,3,3,3-hexafluoropropane (HFC-236fa). The process comprises (a) reacting HF and at least one halopropene of the formula $CX_3CCl=CClX$, wherein each X is independently selected from the group consisting of F and Cl, to produce a product comprising $CF_3CCl=CF_2$ and $CF_3CHClCF_3$, wherein said $CF_3CCl=CF_2$ and $CF_3CHClCF_3$ are produced in the presence of a fluorination catalyst comprising at least one composition selected from the group consisting of (i) compositions comprising $ZnCr_2O_4$ and crystalline α-chromium oxide, (ii) compositions comprising a zinc halide and α-chromium oxide and (iii) compositions of (i) or (ii) which have been treated with a fluorinating agent (e.g., anhydrous hydrogen fluoride); (b) reacting $CF_3CCl=CF_2$ and $CF_3CHClCF_3$ produced in (a) with hydrogen ($H_2$), optionally in the presence of HF, to produce a product comprising $CF_3CH_2CHF_2$ and $CF_3CH_2CF_3$; and (c) recovering $CF_3CH_2CHF_2$ and $CF_3CH_2CF_3$ from the product produced in (b).

DETAILED DESCRIPTION

This invention provides a process for the preparation of $CF_3CH_2CHF_2$ (HFC-245fa) and $CF_3CH_2CF_3$ (HFC-236fa). The HFC-245fa and HFC-236fa may be recovered as individual products and/or as one or more mixtures of the two products.

In step (a) of the process of this invention, one or more halopropene compounds $CX_3CCl=CClX$, wherein each X is independently selected from the group consisting of F and Cl, are reacted with hydrogen fluoride (HF) to produce a product mixture comprising $CF_3CCl=CF_2$ (CFC-1215xc) and $CF_3CHClCF_3$ (HCFC-226da). Accordingly, this invention provides a process for the preparation of mixtures of $CF_3CCl=CF_2$ (CFC-1215xc) and $CF_3CHClCF_3$ (HCFC-226da) from readily available starting materials.

Suitable starting materials for the process of this invention include E-and Z-$CF_3CCl=CClF$ (CFC-1214xb), $CF_3CCl=CCl_2$ (CFC-1213xa), $CClF_2CCl=CCl_2$ (CFC-1212xa), $CCl_2FCCl=CCl_2$ (CFC-1211xa), and $CCl_3CCl=CCl_2$ (hexachloropropene, HCP), or mixtures thereof.

Due to their availability, $CF_3CCl=CCl_2$ (CFC-1213xa) and $CCl_3CCl=CCl_2$ (hexachloropropene, HCP) are the preferred starting materials for the process of the invention.

Preferably, the reaction of HF with $CX_3CCl=CClX$ is carried out in the vapor phase in a heated tubular reactor. A number of reactor configurations are possible, including vertical and horizontal orientation of the reactor and different modes of contacting the halopropene starting material(s) with HF. Preferably the HF is substantially anhydrous.

In one embodiment of step (a), the halopropene starting material(s) may be fed to the reactor containing the fluorination catalyst. The halopropene starting material(s) may be initially vaporized and fed to the reactor as gas(es).

In another embodiment of step (a), the halopropene starting material(s) may be contacted with HF in a pre-reactor. The pre-reactor may be empty (i.e., unpacked), but is preferably filled with a suitable packing such as Monel™ or Hastelloy™ nickel alloy turnings or wool, or other material inert to HCl and HF which allows efficient mixing of $CX_3CCl=CClX$ and HF.

If the halopropene starting material(s) are fed to the pre-reactor as liquid(s), it is preferable for the pre-reactor to be oriented vertically with $CX_3CCl=CClX$ entering the top of the reactor and pre-heated HF vapor introduced at the bottom of the reactor.

Suitable temperatures for the pre-reactor are within the range of from about 80° C. to about 250° C., preferably from about 100° C. to about 200° C. Under these conditions, for example, hexachloropropene is converted to a mixture containing predominantly CFC-1213xa. The starting material feed rate is determined by the length and diameter of the reactor, the temperature, and the degree of fluorination desired within the pre-reactor. Slower feed rates at a given temperature will increase contact time and tend to increase the amount of conversion of the starting material and increase the degree of fluorination of the products.

The term "degree of fluorination" means the extent to which fluorine atoms replace chlorine substituents in the $CX_3CCl=CClX$ starting materials. For example, $CF_3CCl=CClF$ represents a higher degree of fluorination than $CClF_2CCl=CCl_2$ and $CF_3CHClCF_3$ represents a higher degree of fluorination than $CClF_2CHClCF_3$.

The molar ratio of HF fed to the pre-reactor, or otherwise to the reaction zone of step (a), to halopropene starting material fed in step (a), is typically from about stoichiometric to about 50:1. The stoichiometric ratio depends on the average degree of fluorination of the halopropene starting material(s) fed to the pre-reactor and is typically based on formation of $C_3ClF_5$. For example, if the halopropene is HCP, the stoichiometric ratio of HF to HCP is 5:1; if the halopropene is CFC-1213xa, the stoichiometric ratio of HF to CFC-1213xa is 2:1. Preferably, the molar ratio of HF to halopropene starting material is from about twice the stoichiometric ratio (based on formation of $C_3ClF_5$) to about 30:1. Higher ratios than 30:1 are not particularly beneficial. Lower ratios of HF to halopropene result in reduced yields of CFC-1215xc and HCFC-226da. Typically, for a given catalyst, higher HF feed ratios will tend to favor formation of HCFC-226da relative to CFC-121 5xc.

In a preferred embodiment of this invention, in step (a) of the process, the halopropene starting materials are vaporized, preferably in the presence of HF, contacted with HF in a pre-reactor, and then contacted with the fluorination catalyst. If the preferred amount of HF is fed in the pre-reactor, additional HF is not required when the effluent from the pre-reactor contacts the fluorination catalyst.

Suitable temperatures for catalytic fluorination of halopropene starting materials and/or their products formed in the pre-reactor are within the range of about 200° C. to about 400° C., preferably from about 240° C. to about 350° C. Higher temperatures typically contribute to reduced catalyst life. Temperatures below about 240° C. may result in substantial amounts of products having a degree of fluorination less than five (i.e., underfluorinates). Suitable reactor pressures for vapor phase embodiments of this invention may be in the range of from about 1 to about 30 atmospheres. Reactor pressures of about 5 atmospheres to about 20 atmospheres may be advantageously employed to facilitate separation of HCl from other reaction products in step (b) of the process.

The fluorination catalysts which are used in the process of the present invention are preferably compositions comprising $ZnCr_2O_4$ (zinc chromite) and crystalline $\alpha\text{-}Cr_2O_3$ ($\alpha$-chromium oxide) or compositions obtained by treatment of said compositions comprising $ZnCr_2O_4$ (zinc chromite) and crystalline $\alpha\text{-}Cr_2O_3$ ($\alpha$-chromium oxide) with a fluorinating agent. The amount of zinc relative to the total of chromium and zinc in these compositions is preferably from about 1 atom % to about 25 atom %.

Of note are chromium-containing catalyst compositions comprising $ZnCr_2O_4$ (zinc chromite) and crystalline $\alpha$-chromium oxide wherein the $ZnCr_2O_4$ contains between about 10 atom percent and 67 atom percent of the chromium in the composition and at least about 70 atom percent of the zinc in the composition, and wherein at least about 90 atom percent of the chromium present as chromium oxide in the composition is present as $ZnCr_2O_4$ or crystalline $\alpha$-chromium oxide. Also of note are chromium-containing catalyst compositions, prepared by treatment of such compositions comprising $ZnCr_2O_4$ and crystalline $\alpha$-chromium oxide with a fluorinating agent. Also of note are such chromium-containing catalyst compositions which comprise $ZnCr_2O_4$ and crystalline $\alpha$-chromium oxide wherein the $ZnCr_2O_4$ contains between about 20 atom percent and about 50 atom percent of the chromium in the composition. Also of note are such chromium-containing catalyst compositions which comprise $ZnCr_2O_4$ and crystalline $\alpha$-chromium oxide wherein the $ZnCr_2O_4$ contains at least about 90 atom percent of the zinc in the composition. Also of note are such chromium-containing catalyst compositions comprising zinc chromite and crystalline $\alpha$-chromium oxide wherein greater than 95 atom percent of 35 the chromium that is not present as zinc chromite is present as crystalline $\alpha$-chromium oxide. Also of note are such chromium-containing catalyst compositions which consist essentially of $ZnCr_2O_4$ (zinc chromite) and crystalline $\alpha$-chromium oxide.

These compositions may be prepared, for example, by co-precipitation methods followed by calcination.

In a typical co-precipitation procedure, an aqueous solution of zinc and chromium(III) salts is prepared. The relative concentrations of the zinc and chromium(III) salts in the aqueous solution is dictated by the bulk atom percent zinc relative to chromium desired in the final catalyst. Therefore, the concentration of zinc in the aqueous solution is from about 1 mole % to about 25 mole % of the total concentration of zinc and chromium in the solution. The concentration of chromium(III) in the aqueous solution is typically in the range of 0.3 to 3 moles per liter with 0.75-1.5 moles per liter being a preferred concentration. While different chromium (III) salts might be employed, chromium(III) nitrate or its hydrated forms such as $[Cr(NO_3)_3(H_2O)_9]$, are the most preferred chromium(III) salts for preparation of said aqueous solution.

While different zinc salts might be employed for preparation of said aqueous solutions, preferred zinc salts for preparation of catalysts for the process of this invention include zinc(II) nitrate and its hydrated forms such as $[Zn(NO_3)_2(H_2O)_6]$.

The aqueous solution bf the chromium(III) and zinc salts may then be evaporated either under vacuum or at elevated temperature to give a solid which is then calcined.

It is preferred to treat the aqueous solution of the chromium(III) and zinc salts with a base such as ammonium hydroxide (aqueous ammonia) to precipitate the zinc and chromium as the hydroxides. Bases containing alkali metals such as sodium or potassium hydroxide or the carbonates may be used but are not preferred. The addition of ammonium hydroxide to the aqueous solution of the chromium (III) and zinc salts is typically carried out gradually over a period of 1 to 12 hours. The pH of the solution is monitored during the addition of base. The final pH is typically in the range of 6.0 to 11.0, preferably from about 7.5 to about 9.0, most preferably about 8.0 to about 8.7. The precipitation of the zinc and chromium hydroxide mixture is typically carried out at a temperature of about 15° C. to about 60° C., preferably from about 20° C. to about 40° C. After the ammonium hydroxide is added, the mixture is typically stirred for up to 24 hours. The precipitated chromium and zinc hydroxides serve as precursors to $ZnCr_2O_4$ and $\alpha$-chromium oxide.

After the precipitation of the zinc and chromium hydroxide mixture is complete, the mixture is dried. This may be carried out by evaporation in an open pan on a hot plate or steam bath or in an oven or furnace at a suitable temperature. Suitable temperatures include temperatures from about 60° C. to about 130° C. (for example, about 100° C. to about 120° C.). Alternatively, the drying step may be carried out under vacuum using, for example, a rotary evaporator.

Optionally, the precipitated zinc and chromium hydroxide mixture may be collected and, if desired, washed with deionized water before drying. Preferably the precipitated zinc and chromium hydroxide mixture is not washed prior to the drying step.

After the zinc and chromium hydroxide mixture has been dried, the nitrate salts are then decomposed by heating the solid from about 250° C. to about 350° C. The resulting solid is then calcined at temperatures of from about 400° C. to about 1000° C., preferably from about 400° C. to about 900° C.

Further information on the zinc and chromium compositions useful for this invention is provided in U. S. Patent Application 60/511,353 filed Oct. 14, 2003, and hereby incorporated by reference herein in its entirety (see also corresponding International Application No. PCT/US2004/034446).

The calcined zinc chromite/α-chromium oxide compositions of the present invention may be pressed into various shapes such as pellets for use in packing reactors. It may also be used in powder form.

Typically, the calcined compositions will be pre-treated with a fluorinating agent prior to use as catalysts for changing the fluorine content of halogenated carbon compounds. Typically this fluorinating agent is HF though other materials may be used such as sulfur tetrafluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the dried, calcined catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pretreatment is not essential.

Other catalysts suitable for the fluorinations of step (a) are compositions comprising a zinc halide and α-chromium oxide and compositions obtained by treatment of said compositions comprising a zinc halide and α-chromium oxide with a fluorinating agent. U.S. Pat. No. 3,878,257 discloses an example of such catalysts. The amount of zinc relative to the total of chromium and zinc in these compositions is preferably from about 0.1 atom % to about 25 atom %; and is more preferably from about 2 atom % to about 10 atom %. Of note are compositions wherein a zinc halide is supported on a support comprising α-chromium oxide. Preferably, the α-chromium oxide is prepared according to U.S. Pat. No. 5,036,036. Pretreatment with a fluorinating agent can be carried out as indicated above for the calcined zinc chromite/α-chromium oxide compositions.

Compounds that are produced in the fluorination process in step (a) include the $CF_3CCl=CF_2$ (CFC-1215xc) and $CF_3CHClCF_3$ (HCFC-226da).

Halopropane by-products having a higher degree of fluorination than HCFC-226da that may be formed in step (a) include $CF_3CClFCF_3$ (CFC-217ba).

Halopropane by-products having a lower degree of fluorination than HCFC-226da that may be formed in step (a) include $CF_3CHClCClF_2$ (HCFC-225da). Other halopropane by-products which may be formed include CFC-216aa ($CF_3CCl_2CF_3$).

Halopropene by-products having a lower degree of fluorination than CFC-1215xc that may be formed in step (a) include E- and Z-$CF_3CCl=CClF$ (CFC-1214xb) and $CF_3CCl=CCl_2$ (CFC-1213xa).

Typically, the effluent from step (a) comprising CFC-1215xc and HCFC-226da, and optionally HF, is separated from lower boiling components, mainly comprising HCl along with some over-fluorinated products such as CFC-217ba and azeotropic HF, and from the higher boiling components comprising the under-fluorinated components such as HCFC-225da, $C_3Cl_4F_4$ isomers, and CFC-1213xa.

In one embodiment of the process of this invention, the reactor effluent from step (a) may be delivered to a distillation column in which HCl and any HCl azeotropes are removed from the top of column while the higher boiling components are removed at the bottom of the column. The products recovered at the bottom of the first distillation column are then delivered to a second distillation column in which CFC-217ba, and some HF, are separated at the top of the column and the remaining HF and organic products, comprising $CF_3CHClCF_3$, $CF_3CCl=CF_2$, and higher boiling components, are removed from the bottom of the column. The products recovered from the bottom of the second distillation column are then delivered to a third distillation column in which $CF_3CHClCF_3$, $CF_3CCl=CF_2$, and HF, are separated at the top of the column, and any remaining HF and under-fluorinated components are removed from the bottom of the column.

The mixture of $CF_3CHClCF_3$, $CF_3CCl=CF_2$, and HF, from the top of the third distillation column may be delivered to step (b) or may optionally be delivered to a decanter maintained at a suitable temperature to cause separation of an organic-rich liquid phase and an HF-rich liquid phase.

The HF-rich phase may be distilled to recover HF which is then recycled to step (a). The organic-rich phase may then be delivered to step (b) or may be distilled to give pure HCFC-226da and CFC-1215xc.

In one embodiment of the process of this invention said under-flourinated components such as HCFC-225da, $C_3Cl_2F_4$, and $CF_3CCl=CCl_2$ (CFC-1213xa) may be returned to step (a).

In step (b) of the process, the $CF_3CHClCF_3$ and $CF_3CCl=CF_2$ produced in step (a) are reacted with hydrogen ($H_2$), optionally in the presence of HF.

In one embodiment of step (b), a mixture comprising $CF_3CHClCF_3$ and $CF_3CCl=CF_2$, and optionally HF, is delivered in the vapor phase, along with hydrogen ($H_2$), to a reactor fabricated from nickel, iron, titanium, or their alloys, as described in U.S. Pat. No. 6,540,933; the teachings of this disclosure are incorporated herein by reference. A reaction vessel of these materials (e.g., a metal tube) optionally packed with the metal in suitable form may also be used. When reference is made to alloys, it is meant a nickel alloy containing form 1 to 99.9% (by weight) nickel, an iron alloy containing 0.2 to 99.8% (by weight) iron, and a titanium alloy containing 72-99.8% (by weight) titanium. Of note is use of an empty (unpacked) reaction vessel made of nickel or alloys of nickel such as those containing 40% to 80% nickel, e.g., Inconel™ 600 nickel alloy, Hastelloy™ C617 nickel alloy, or Hastelloy™ C276 nickel alloy.

When used for packing, the metal or metal alloys may be particles or formed shapes such as perforated plates, rings, wire, screen, chips, pipe, shot, gauze, or wool.

The temperature of the reaction in this embodiment can be between about 35° C. and about 600° C., and is preferably at least about 450° C.

The molar ratio of hydrogen to the CFC-1215xc/HCFC-226da mixture fed to the reaction zone should be in the range of about 0.1 mole $H_2$ per mole of CFC-1215xc/HCFC-226da mixture to about 60 moles of $H_2$ per mole of CFC-1215xc/HCFC-226da mixture, more preferably from about 0.4 to 10 moles of $H_2$ per mole of CFC-1215xc/HCFC-226da mixture.

In another embodiment of the process, the contacting of hydrogen with the CFC-1215xc/HCFC-226da mixture produced in step (a), and optionally HF, is carried out in the presence of a hydrogenation catalyst. Hydrogenation catalysts suitable for use in this embodiment include catalysts comprising at least one metal selected from the group consisting of rhenium, iron, ruthenium, osmium, cobalt, rhodium, iridium, nickel, palladium, and platinum. Said catalytic metal component is typically supported on a carrier such as carbon or graphite or a metal oxide, fluorinated metal oxide, or metal fluoride where the carrier metal is selected from the group consisting of magnesium, aluminum, titanium, vanadium, chromium, iron, and lanthanum.

Of note are carbon supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference. Also of note are catalysts comprising at least one metal selected from the group consisting of palladium, platinum, and rhodium supported on alumina ($Al_2O_3$), fluorinated alumina, or aluminum fluoride ($AlF_3$).

The supported metal catalysts may be prepared by conventional methods known in the art such as by impregnation of the carrier with a soluble salt of the catalytic metal (e.g., palladium chloride or rhodium nitrate) as described by Satterfield on page 95 of *Heterogenous Catalysis in Industrial Practice*, $2^{nd}$ edition (McGraw-Hill, N.Y., 1991). The concentration of the catalytic metal(s) on the support is typically in the range of about 0.1% by weight of the catalyst to about 5% by weight.

The relative amount of hydrogen contacted with CFC-1215xc and HCFC-226da when a hydrogenation catalyst is used is typically from about the stoichiometric ratio of hydrogen to $CF_3CHClCF_3/CF_3CCl=CF_2$ mixture to about 10 moles of $H_2$ per mole of $CF_3CHClCF_3/CF_3CCl=CF_2$ mixture. The stoichiometric ratio of hydrogen to the $CF_3CHClCF_3/CF_3CCl=CF_2$ mixture depends on the relative amounts of the two components in the mixture. The stoichiometric amounts of $H_2$ required to convert HCFC-226da and CFC-1215xc to $CF_3CH_2CF_3$ and $CF_3CH_2CHF_2$, are one and two moles, respectively.

Suitable temperatures for the catalytic hydrogenation are typically from about 100° C. to about 350° C., preferably from about 125° C. to about 300° C. Temperatures above about 350° C. tend to result in defluorination side reactions; temperatures below about 125° C. will result in incomplete substitution of Cl for H in the starting materials. The reactions are typically conducted at atmospheric pressure or superatmospheric pressure.

The products from the step (b) reaction zone(s) typically include HCl, $CF_3CH_2CF_3$ (HFC-236fa), $CF_3CH_2CHF_2$ (HFC-245fa), and small amounts of lower boiling by-products (typically including propane, $CF_3CH=CF_2$ (HFC-1225zc), E-and Z-$CF_3CH=CHF$ (HFC-1234ze), and/or $CF_3CH_2CH_3$ (HFC-263fb)) and higher boiling by-products and intermediates (typically including $CF_3CHFCH_3$ (HFC-254eb) and/or $CF_3CHClCHF_2$ (HCFC-235da)) as well as any unconverted starting materials and any HF carried over from step (a).

In step (c), the desired products are recovered. Products from step (b) may be delivered to a separation unit to recover $CF_3CH_2CF_3$ and $CF_3CH_2CHF_2$ individually, as a mixture, or as their HF azeotropes.

Partially chlorinated components such as HCFC-235da may be recovered and recycled back to step (b).

The reactor, distillation columns, and their associated feed lines, effluent lines, and associated units used in applying the processes of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific embodiments are to be construed as merely illustrative, and do not constrain the remainder of the disclosure in any way whatsoever.

EXAMPLES

| LEGEND | |
|---|---|
| 215aa is $CF_3CCl_2CClF_2$ | 216aa is $CF_3CCl_2CF_3$ |
| 217ba is $CF_3CClFCF_3$ | 225da is $CF_3CHClCClF_2$ |
| 226da is $CF_3CHClCF_3$ | 1213xa is $CF_3CCl=CCl_2$ |
| 1214 is $C_3Cl_2F_4$ | 1215xc is $CF_3CCl=CF_2$ |

Catalyst Preparation

Comparative Preperation Example 1

Preparation of 100% Chromium Catalyst (400° C.)

A solution of 400 g $Cr(NO_3)_3[9(H_2O)]$ (1.0 mole) in 1000 mL of deionized water was treated dropwise with 477 mL of 7.4M aqueous ammonia raising the pH to about 8.5. The slurry was stirred at room temperature overnight. After re-adjusting the pH to 8.5 with ammonia, the mixture was poured into evaporating dishes and dried in air at 120° C. The dried solid was then calcined in air at 400° C.; the resulting solid weighed 61.15 g. The catalyst was pelletized (−12 to +20 mesh, (1.68 to 0.84 mm)) and 28.2 g (20 mL) was used in Comparative Example 1.

Comparative Preperation Example 2

Preparation of 2% Zinc on Alumina Catalyst

Aluminum oxide (4.90 moles, Harshaw 3945, dried at 110° C.) was added to a solution of 20.85 g $ZnCl_2$ (0.153 mole) dissolved in 460 mL of distilled water. Water was evaporated from the mixture with stirring and then dried at 110° C. for three days. The catalyst was pelletized (−12 to +20 mesh, (1.68 to 0.84 mm)) and 21.1 g (30 mL) was used in Comparative Example 3.

Preperation Example 1

Preparation of 2% Zinc Chloride Supported on Chromium Oxide

A solution of 1.20 g $ZnCl_2$ (8.81 moles) in 60 mL of deionized water 30 contained in a 125 mm×65 mm glass dish was treated with 60.00 g (0.357 mole) of 12-20 mesh $Cr_2O_3$. The dish was placed on a warm hot plate and the slurry allowed to dry with occasional stirring. The resulting solid was then dried overnight at 130° C.; the resulting solid weighed 60.42 g. The catalyst was pelletized (−12 to +20 mesh, (1.68 to 0.84 mm)) and 41.5 g (30 mL) was used in Example 1.

Preperation Example 2

Preperation of 95% Chromium/5% Zinc Catalyst (450° C.)

A solution of 380.14 g $Cr(NO_3)_3[9(H_2O)]$ (0.950 mole) and 14.87 g $Zn(NO_3)_2[6(H_2O)]$ (0.050 mole) was prepared in 1000 mL of deionized water. The solution was treated with 450 mL of 7.4M aqueous ammonium hydroxide over the course of one hour; the pH increased from 1.7 to pH 8.4. The slurry was stirred at room temperature overnight and then dried at 120° C. in an oven in the presence of air. The dried solid was then calcined in air at 450° C. for 20 hours; the resulting solid weighed 76.72 g. The catalyst was pelletized (−12 to +20 mesh, (1.68 to 0.84 mm)) and 38.5 g (25 mL) was used in Example 6.

Preperation Example 3

Preparation of 90% Chromium/10% Zinc Catalyst (900° C.)

A solution of 360.13 g $Cr(NO_3)_3[9(H_2O)]$ (0.900 mole) and 29.75 g $Zn(NO_3)_2[6(H_2O)]$ (0.100 mole) was prepared in 1000 mL of deionized water. The solution was treated with 450 mL of 7.4M aqueous ammonium hydroxide over the course of 1.4 hours; the pH increased from 1.9 to pH 8.4. The slurry was stirred at room temperature overnight and then dried at 120° C. in the presence of air. The dried solid was then calcined in air at 900° C. for 20 hours; the resulting solid weighed 75.42 g. The catalyst was pelletized (−12 to +20 mesh, (1.68 to 0.84 mm)) and 42.3 g (25 mL) was used in Example 8.

Preperation Example 4

Preparation of 95% Chromium/5% Zinc Catalyst (900° C.)

A solution of 380.14 g $Cr(NO_3)_3[9(H_2O)]$ (0.950 mole) and 14.87 g $Zn(NO_3)_2[6(H_2O)]$ (0.050 mole) was prepared in 1000 mL of deionized water. The solution was treated with 450 mL of 7.4M aqueous ammonium hydroxide over the course of one hour; the pH increased from 1.7 to pH 8.4. The slurry was stirred at room temperature overnight and then dried at 120° C. in an oven in the presence of air. The dried solid was then calcined in air at 900° C. for 20 hours; the resulting solid weighed 70.06 g.

The catalyst was pelletized (−12 to +20 mesh, (1.68 to 0.84 mm)) and 25.3 g (14 mL) was used in Example 7.

Preperation Example 5

Preparation of 98% Chromium/2% Zinc Catalyst (900° C.)

A solution of 392.15 g $Cr(NO_3)_3[9(H_2O)]$ (0.980 mole) and 5.94 g $Zn(NO_3)_2[6(H_2O)]$ (0.020 mole) was prepared in 1000 mL of deionized water. The solution was treated with 450 mL of 7.4M aqueous ammonium hydroxide over the course of 0.58 hour; the pH increased from 1.67 to pH 8.35. The slurry was stirred at room temperature overnight and then dried at 120° C. in an oven in the presence of air. The dried solid was then calcined in air at 900° C. for 21 hours; the resulting solid weighed 66.00 g. The catalyst was pelletized (−12 to +20 mesh, (1.68 to 0.84 mm)) and 44.9 g (23 mL) was used in Example 5.

Preperation Example 6

Preparation of 10% Zinc Chloride Supported on Chromium Oxide

A solution of 6.0 g $ZnCl_2$ (44 moles) in 300 mL of deionized water contained in a 170 mm×90 mm glass dish was treated with 60.00 g (0.357 mole) of 12-20 mesh $Cr_2O_3$. The dish was placed on a warm hot plate and the slurry allowed to dry with occasional stirring. The resulting solid was then dried overnight at 130° C.; the resulting solid weighed 65.02 g. The catalyst was pelletized (−12 to +20 mesh, (1.68 to 0.84 mm)) and 37.5 g (25 mL) was used in Example 2.

Preperation Example 7

Preparation of 98.1% Chromium/1.9% Zinc Catalyst (550° C.)

A solution of 516.46 g $Cr(NO_3)_3[9(H_2O)]$ (1.29 moles) and 7.31 g $Zn(NO_3)_2[6(H_2O)]$ (0.0246 mole) was prepared in 500 mL of distilled water in 1L beaker resting on a hot plate. The mixture was then transferred to a Pyrex™ container and the container placed in a furnace. The container was heated from room temperature to 125° C. at 10° C./min and then held at 125° C. for six hours. The container was heated from 125° C. to 350° C. at 1° C./min and then held at 350° C. for six hours. The container was heated from 350° C. to 550° C. at 1° C./min and then held at 550° C. for 24 hours. The catalyst was pelletized (−12 to +20 mesh, (1.68 to 0.84 mm)) and 29.9 g (20 mL) was used in Examples 3 and 4.

Examples 1-8 and Comparative Examples 1-3

General Procedure for Fluorination

A weighed quantity of pelletized catalyst was placed in a 5/8" (1.58 cm) diameter Inconel™ nickel alloy reactor tube heated in a fluidized sand bath. The tube was heated from 50° C. to 175° C. in a flow of nitrogen (50 cc/min; $8.3(10)^{-7} m^3$/sec) over the course of about one hour. HF was then admitted to the reactor at a flow rate of 50 cc/min ($8.3(10)^{-7} m^3$/sec). After 0.5 to 2 hours the nitrogen flow was decreased to 20 cc/min ($3.3(10)^{-7} m^3$/sec) and the HF flow increased to 80 cc/min ($1.3(10)^{-6} m^3$/sec); this flow was maintained for about 1 hour. The reactor temperature was then gradually increased to 400° C. over 3 to 5 hours. At the end of this period, the HF flow was stopped and the reactor cooled to 300° C. under 20 sccm ($3.3(10)^{-7} m^3$/sec) nitrogen flow. CFC-1213xa was fed from a pump to a vaporizer maintained at about 118° C. The CFC-1213xa vapor was combined with the appropriate molar ratios of HF in a 0.5 inch (1.27 cm) diameter Monel™ nickel alloy tube packed with Monel™ turnings. The mixture of reactants then entered the reactor; the contact time was 15 seconds unless otherwise indicated. All reactions were conducted at a nominal pressure of one atmosphere. The results of CFC-1213xa fluorination over the several catalysts are shown in Table 1; analytical data is given in units of GC area %.

TABLE 1

| Exa. No. | HF/1213 Ratio | Temp ° C. | Catalyst | Products, GC Area % ||||||| 
|---|---|---|---|---|---|---|---|---|---|---|
| | | | | 1215xc | 217ba | 226da | 216aa | 225da | 1214's | 1213xa |
| 1[a] | 20/1 | 260 | 2% $ZnCl_2/Cr_2O_3$ | 65.9 | — | 19.9 | 0.9 | 1.60 | 3.3 | 4.8 |
| 2[a] | 6/1 | 280 | 10% $ZnCl_2/Cr_2O_3$ | 42.4 | — | 1.2 | 0.04 | 2.8 | 15.4 | 37.7 |
| 3[b] | 20/1 | 300 | Cr/Zn 98.1/1.9 550° C. | 20.1 | 0.3 | 64.2 | 9.1 | 1.6 | 1.6 | 0.8 |
| 4 | 20/1 | 350 | Cr/Zn 98.1/1.9 550° C. | 7.9 | 0.4 | 77.2 | 11.2 | 0.2 | 0.7 | 0.4 |
| 5 | 6/1 | 280 | Cr/Zn 98/2 900° C. | 34.8 | — | 1.1 | 0.04 | 2.5 | 16.4 | 44.6 |
| 6[b] | 6/1 | 280 | Cr/Zn 95/5 450° C. | 1.3 | 0.01 | 73.0 | 6.5 | 0.4 | 1.3 | 1.5 |
| 7 | 30/1 | 320 | Cr/Zn 95/5 900° C. | 79.0 | — | 5.9 | 0.3 | — | 4.0 | 8.7 |

TABLE 1-continued

| Exa. No. | HF/1213 Ratio | Temp °C. | Catalyst | Products, GC Area % | | | | | | |
|---|---|---|---|---|---|---|---|---|---|---|
| | | | | 1215xc | 217ba | 226da | 216aa | 225da | 1214's | 1213xa |
| 8 | 20/1 | 280 | Cr/Zn 90/10 900° C. | 70.3 | — | 10.2 | 1.0 | 3.1 | 8.1 | 6.6 |
| C1[c] | 20/1 | 300 | 100% $Cr_2O_3$ | 0.3 | 0.9 | 89.7 | 7.8 | — | 8.1 | 6.6 |
| C2[a,c,d] | 20/1 | 300 | 100% $Cr_2O_3$ (HSA) | 0.2 | — | 94.5 | 3.9 | — | — | — |
| C3[a,c] | 6/1 | 280 | 2% $Zn/Al_2O_3$ | 2.5 | 0.02 | 90.5 | 0.02 | 1.4 | 1.4 | 3.2 |

[a]The contact time was 30 seconds.
[b]Product contained 12.8 GC area % CFC-215aa.
[c]Comparative Example.
[d]High surface area chromium oxide from a commercial source; the catalyst was activated with HF prior to use following the general procedure.

What is claimed is:

1. A process for the manufacture of 1,1,1,3,3-pentafluoropropane and 1,1,1,3,3,3-hexafluoropropane, comprising:
    (a) reacting HF and at least one halopropene of the formula $CX_3CCl=CClX$, wherein each X is independently selected from the group consisting of F and Cl, to produce a product comprising $CF_3CCl=CF_2$ and $CF_3CHClCF_3$, wherein said $CF_3CCl=CF_2$ and $CF_3CHClCF_3$ are produced in the presence of a fluorination catalyst comprising at least one composition selected from the group consisting of (i) compositions comprising $ZnCr_2O_4$ and crystalline α-chromium oxide, (ii) compositions comprising a zinc halide and α-chromium oxide and (iii) compositions of (i) or (ii) which have been treated with a fluorinating agent;
    (b) reacting $CF_3CCl=CF_2$ and $CF_3CHClCF_3$ produced in (a) with hydrogen to produce a product comprising $CF_3CH_2CHF_2$ and $CF_3CH_2CF_3$; and
    (c) recovering $CF_3CH_2CHF_2$ and $CF_3CH_2CF_3$ from the product produced in (b).

2. The process of claim 1 wherein in (a) the catalyst is selected from the group consisting of (i) compositions comprising $ZnCr_2O_4$ and crystalline α-chromium oxide and (iii) compositions of (i) which have been treated with a fluorinating agent.

3. The process of claim 2 wherein the amount of zinc relative to the total of chromium and zinc in the catalyst composition is from about 1 atom % to about 25 atom %.

4. The process of claim 2 wherein the catalyst is selected from the group consisting of (i) compositions comprising $ZnCr_2O_4$ and crystalline α-chromium oxide wherein the $ZnCr_2O_4$ contains between about 10 atom percent and 67 atom percent of the chromium in the composition and at least about 70 atom percent of the zinc in the composition, and wherein at least about 90 atom percent of the chromium present as chromium oxide in the composition is present as $ZnCr_2O_4$ or crystalline α-chromium oxide and (iii) compositions of (i) which have been treated with a fluorinating agent.

5. The process of claim 1 wherein in (a) the catalyst is selected from the group consisting of (ii) compositions comprising a zinc halide and α-chromium oxide and (iii) compositions of (ii) which have been treated with a fluorinating agent.

6. The process of claim 5 wherein the amount of zinc relative to the total of chromium and zinc in the catalyst composition is from about 0.1 atom % to about 25 atom %.

7. The process of claim 5 wherein the catalyst is selected from the group consisting of (ii) compositions wherein a zinc halide is supported on a support comprising α-chromium oxide and (iii) compositions of (ii) which have been treated with a fluorinating agent; and wherein the amount of zinc relative to the total of chromium and zinc in the catalyst composition is from about 2 atom % to about 10 atom %.

* * * * *